United States Patent
Ertel et al.

(10) Patent No.: US 10,908,244 B2
(45) Date of Patent: Feb. 2, 2021

(54) DETERMINING TWO-DIMENSIONAL IMAGE DATA FROM AT LEAST ONE SECTIONAL SURFACE OF AN ACQUISITION VOLUME AS PART OF A MAGNETIC RESONANCE IMAGING PROCESS

(71) Applicants: Dirk Ertel, Forchheim (DE); Yiannis Kyriakou, Spardorf (DE)

(72) Inventors: Dirk Ertel, Forchheim (DE); Yiannis Kyriakou, Spardorf (DE)

(73) Assignee: Siemens Healthcare GmbH, Erlangen (DE)

( * ) Notice: Subject to any disclaimer, the term of this patent is extended or adjusted under 35 U.S.C. 154(b) by 645 days.

(21) Appl. No.: 15/663,749

(22) Filed: Jul. 29, 2017

(65) Prior Publication Data

US 2018/0031655 A1 Feb. 1, 2018

(30) Foreign Application Priority Data

Jul. 29, 2016 (DE) .................... 10 2016 214 061

(51) Int. Cl.
*G01R 33/48* (2006.01)
*A61B 6/00* (2006.01)
(Continued)

(52) U.S. Cl.
CPC ........ *G01R 33/4812* (2013.01); *A61B 5/0035* (2013.01); *A61B 5/055* (2013.01);
(Continued)

(58) Field of Classification Search
CPC ............ G01R 33/4812; G01R 33/4833; G01R 33/5608; G01R 33/286; G01R 33/34;
(Continued)

(56) References Cited

U.S. PATENT DOCUMENTS 5,524,086 A * 6/1996 Kiyuna .................... G06N 3/04
702/57
10,507,339 B2 * 12/2019 Filiberti ............... A61N 5/1045
(Continued)

FOREIGN PATENT DOCUMENTS

CN 1973297 A 5/2007
CN 101522134 A 9/2009
(Continued)

OTHER PUBLICATIONS

Elayaperumal, Santhi, et al. "Autonomous real-time interventional scan plane control with a 3-D shape-sensing needle." IEEE transactions on medical imaging 33.11 (2014): 2128-2139.
(Continued)

*Primary Examiner* — Sanjay Cattungal
(74) *Attorney, Agent, or Firm* — Lempia Summerfield Katz LLC

(57) ABSTRACT

A method for determining two-dimensional image data from at least one sectional surface of an acquisition volume as part of a magnetic resonance imaging process by a combined apparatus, including a magnetic resonance imaging facility and an X-ray facility, is provided. The method includes controlling the X-ray facility to acquire at least one X-ray image that images at least part of an object. At least one piece of object information is determined by image processing the X-ray image. At least one sectional-surface parameter that defines an arrangement of the sectional surface in the acquisition volume is determined. The magnetic resonance imaging facility is controlled to acquire measurement data relating to the sectional surface. The two-dimensional image data is calculated from the measurement data. The sectional-surface parameter is used as the basis for the control of the magnetic resonance imaging facility and/or for the calculation of the two-dimensional image data.

22 Claims, 3 Drawing Sheets

(51) Int. Cl.
*A61B 5/055* (2006.01)
*A61B 5/00* (2006.01)
*A61B 5/06* (2006.01)
*G01R 33/483* (2006.01)
*A61B 6/12* (2006.01)
*G01R 33/28* (2006.01)
*G01R 33/56* (2006.01)

(52) U.S. Cl.
CPC .................. *A61B 5/06* (2013.01); *A61B 6/12* (2013.01); *A61B 6/4417* (2013.01); *A61B 6/5247* (2013.01); *G01R 33/4833* (2013.01); *A61B 6/504* (2013.01); *G01R 33/286* (2013.01); *G01R 33/5608* (2013.01)

(58) Field of Classification Search
CPC ........... A61B 5/06; A61B 6/4417; A61B 6/12; A61B 5/0035; A61B 5/055; A61B 6/5247; A61B 6/504; A61B 2034/2065; A61B 6/482; A61B 90/00; A61B 34/20; G06T 2207/10088; G06T 2207/10116; G06T 11/003; G06T 5/50
See application file for complete search history.

(56) References Cited

U.S. PATENT DOCUMENTS

| | | | |
|---|---|---|---|
| 2008/0130825 A1* | 6/2008 | Fu | G06T 7/248 378/8 |
| 2008/0199059 A1* | 8/2008 | Eck | A61B 8/0833 382/128 |
| 2009/0149867 A1* | 6/2009 | Glozman | A61B 17/3478 606/130 |
| 2010/0312094 A1 | 12/2010 | Guttman et al. | |
| 2011/0071537 A1* | 3/2011 | Koga | A61B 17/155 606/103 |
| 2011/0137156 A1 | 6/2011 | Razzaque et al. | |
| 2012/0143045 A1 | 6/2012 | Klingenbeck | |
| 2012/0286786 A1* | 11/2012 | Schellekens | A61B 6/4417 324/322 |
| 2015/0208996 A1* | 7/2015 | Kyriakou | A61B 6/481 600/431 |
| 2015/0247907 A1 | 9/2015 | Heid et al. | |
| 2015/0374260 A1 | 12/2015 | Govari et al. | |
| 2016/0117826 A1* | 4/2016 | Yan | A61B 6/488 348/135 |
| 2016/0217555 A1 | 7/2016 | Ertel et al. | |
| 2017/0128750 A1* | 5/2017 | Filiberti | A61N 5/1045 |
| 2018/0325477 A1* | 11/2018 | Wang | A61B 5/0035 |

FOREIGN PATENT DOCUMENTS

| | | |
|---|---|---|
| CN | 102625669 A | 8/2012 |
| DE | 102010062340 A1 | 6/2012 |
| DE | 1020015201057 A1 | 7/2016 |
| WO | WO2013104420 A1 | 7/2013 |
| WO | 2014044314 A1 | 3/2014 |

OTHER PUBLICATIONS

Elgort D. et al. "A Method for Realtime Automated Scan Plane Selection"; Proceedings of the International Society for Magnetic Resonance in Medicine, 10th Scientific Meeting and Exhibition, (May 18, 2002).

European Search Report for corresponding Application No. 17179936. 4-1568 / 3217187, dated Jan. 5, 2018.

Fahrig, Rebecca, et al. "A truly hybrid interventional MR/X-ray system: Feasibility demonstration." Journal of Magnetic Resonance Imaging 13.2 (2001): 294-300.

Pan, L., et al. "An integrated system for catheter tracking and visualization in MR-guided cardiovascular interventions." Proceedings of the 19th Annual Meeting of ISMRM. 2011.

Wang, Ge, et al. "Vision 20/20: Simultaneous CT-MRI—Next chapter of multimodality imaging." Medical physics 42.10 (2015): 5879-5889.

German Office Action for German Application No. 102016214061. 2, dated May 3, 2017, with English Translation.

Chinese Office Action and Search Report for Chinese Application No. 20171062242.1 dated Nov. 21, 2019, with English translation.

\* cited by examiner

DETERMINING TWO-DIMENSIONAL IMAGE DATA FROM AT LEAST ONE SECTIONAL SURFACE OF AN ACQUISITION VOLUME AS PART OF A MAGNETIC RESONANCE IMAGING PROCESS

This application claims the benefit of DE 10 2016 214 061.2, filed on Jul. 29, 2016, which is hereby incorporated by reference in its entirety.

BACKGROUND

The present embodiments relate to determining two-dimensional image data from at least one sectional surface of an acquisition volume as part of a magnetic resonance imaging process.

Magnetic resonance imaging devices are frequently used for diagnostic imaging in the medical sector. In addition, however, magnetic resonance imaging devices are also used during interventional procedures in order to assist these procedures using near real-time imaging.

A typical application is assisting a user by employing near real-time magnetic resonance imaging at, for example, at least 5, 10, 20 or 30 images per second in order to visualize for the user an instantaneous situation in a relevant region (e.g., inside a patient). This is particularly applicable when medical instruments (e.g., a catheter) are meant to be guided to a specific position. In this case, near real-time imaging may allow a user to guide the medical instrument accurately on target.

In order to facilitate imaging at a sufficiently high refresh rate, two-dimensional magnetic resonance imaging is typically used here, in which only one slice or only individual slices are excited and the measurement data therefrom acquired and visualized. The problem with this is that the relevant region of a medical instrument (e.g., a catheter tip) may in this situation exit the instantaneously acquired slice, making it necessary to reposition the acquired slice manually. Manual repositioning of the acquired slice by a user constitutes an additional strain on the user and may also extend the time needed for the intervention. A similar problem even arises when volume imaging is used, because the visualization is typically performed for a user in the form of a sectional plane. Thus, even for volume imaging, the displayed sectional plane is repositioned.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method for magnetic resonance imaging that allows, in comparison to the prior art, better repositioning of an acquired measurement slice or of a displayed sectional plane is provided.

In one embodiment, a method for determining two-dimensional image data from at least one sectional surface of an acquisition volume as part of a magnetic resonance imaging process by a combined magnetic resonance imaging and X-ray apparatus including a magnetic resonance imaging facility and an X-ray facility is provided. The coordinate systems thereof that are used for imaging are registered to each other by a mechanical coupling of the X-ray facility to the magnetic resonance imaging facility. The method includes controlling the X-ray facility to acquire at least one X-ray image that images at least part of an object (e.g., a medical instrument). At least one piece of object information that relates to a position and/or an orientation and/or at least one feature of the object is determined by image processing of the X-ray image. At least one sectional-surface parameter that defines an arrangement of the sectional surface in the acquisition volume is determined based on the object information. The magnetic resonance imaging facility is controlled to acquire measurement data relating to the sectional surface. The two-dimensional image data is calculated from the measurement data. The sectional-surface parameter is used as the basis for the control of the magnetic resonance imaging facility and/or for the calculation of the two-dimensional image data.

The fact that in some facilities both radiographic and magnetic resonance imaging is possible, with the coordinate systems used for the imaging having a defined position with respect to each other (e.g., are registered to one another), is exploited. This may be the case, for example, in MRI angiogram scanners. It is known that X-ray imaging at high image rates is possible with relatively low radiation doses, a fact that is exploited in fluoroscopy, for example. Many objects (e.g., many medical instruments) are imaged at high contrast in X-ray imaging. Thus, even at low X-ray doses, it is easy to recognize specific features of these instruments (e.g., the position of a catheter tip). This fact is exploited by one or more of the present embodiments to reposition the two-dimensional magnetic resonance imaging automatically by obtaining the object information from the X-ray image, and using this information in controlling the magnetic resonance imaging and/or in calculating the image data. A sectional surface selected with regard to the object may be repositioned automatically.

This relieves the strain on a user of the combined magnetic resonance imaging and X-ray apparatus because slice repositioning no longer needs to be performed manually. Compared with slice repositioning based purely on magnetic resonance imaging, the method according to one or more of the present embodiments allows faster and more robust repositioning of the imaging. The calculated two-dimensional image data may be displayed on a display facility, for example. This may be effected directly, although it is also possible to process the two-dimensional image data further first (e.g., in order to overlay additional information).

According to one or more of the present embodiments, the coordinate systems used for imaging are registered to one another. Registration of the coordinate systems used may be rigid, for example, by providing rigid coupling of the magnetic resonance imaging facility and the X-ray facility. For example, an X-ray tube and an X-ray detector may be arranged in a fixed position with respect to the main and gradient magnets of the magnetic resonance imaging facility. With rigid registration, both facilities may use a common coordinate system for imaging.

It is also possible, however, to use non-rigid, automatically adjusted registration. For example, components of the X-ray facility (e.g., the X-ray tube and the X-ray detector) may be mounted on the components of the magnetic resonance imaging facility (e.g., on the magnets), such that the components of the X-ray facility may be displaced and/or tilted with respect to these components. The displacement and/or tilting may be performed manually or by actuators of the combined magnetic resonance imaging and X-ray facility. Sensors that detect the relative displacement and/or tilt may be provided, and/or the relative displacement and/or tilt may be known from a corresponding control of the actuators. Based on the known displacement and/or tilt, the relative position and orientation with respect to each other of the coordinate systems used for the imaging are hence also known at every point in time, whereby these coordinate systems are registered to one another.

This registration allows information to be transferred between these coordinate systems. This information may be, for example, coordinates of a point, specific directions, positions and/or shapes of curves (e.g., lines), and/or surfaces (e.g., planes), and/or information about specific features recognized in the image data. The coordinate system of the magnetic resonance imaging may be, in this context, a three-dimensional spatial coordinate system of the magnetic resonance imaging facility. The coordinate system may be spanned, for example, by the directions of the layer-selection gradient, frequency gradient, and/or phase encoding gradient, or have a defined position with respect to these directions. The coordinate system of the X-ray facility may be defined as a three-dimensional coordinate system, the position and orientation of which is specified by the position and orientation of the X-ray detector and/or of the X-ray source. A coordinate-transfer process may take into account that an acquired X-ray intensity at a detector element depends on the line integral of the absorption coefficient between this detector element and the X-ray source. Thus, if there are no other known boundary conditions, a position of a specific feature recognized in the X-ray image may be determined in a three-dimensional coordinate system associated with the X-ray facility only to the extent that the feature lies on a corresponding connecting line.

In the method according to one or more of the present embodiments, the sectional surface, for example, may be a sectional plane, because this allows the measurement data to be acquired particularly easily. In principle, however, it is also possible to use curved sectional surfaces. The sectional surface may have a slice thickness perpendicular to the sectional surface, over which are integrated magnetic resonance signals of the object and/or of other objects in the acquisition volume. The slice thickness of the sectional surface may equal the slice thickness of a slice excited during the magnetic resonance imaging process. It is also possible, however, that frequency encoding or phase encoding is performed in the direction of the slice selection in the magnetic resonance imaging process, whereby the slice thickness may equal the resolution achieved by this frequency encoding or phase encoding or may be selected to have any greater thickness. The slice thickness may be set to a fixed value or according to the sectional-surface parameter.

The sectional-surface parameter may define a situation (e.g., a position and/or an orientation, or even a shape of a measurement region for which measurement data is acquired). Additionally or alternatively, the sectional-surface parameter may specify the situation in the measurement region of the sectional surface to be displayed. This is advantageous, for example, if image data from a curved sectional surface is meant to be displayed.

In the medical sector, both "passive" and "active" instruments are used in an intervention assisted by magnetic resonance imaging. Passive instruments are configured such that the passive instruments may be used during magnetic resonance imaging without interfering with this process, without heating up or the like. Active instruments are also provided with a way of determining the position of the instruments. For example, this may be effected by radio triangulation of a transceiver provided on the active instrument. The method according to one or more of the present embodiments is advantageous when passive instruments are used, because otherwise, the passive instruments may only be located with difficulty. The method may also be used advantageously in conjunction with active instruments, however, because typically only a single point on these active instruments is located. In this case, the method according to one or more of the present embodiments additionally allows account to be taken of an orientation and/or a possible change in shape, which may occur, for example, with catheters.

An associated point position of at least one measurement point may be determined in the X-ray image as the object information. The associated point lies in a defined position with respect to the at least partial image of the object, whereby the sectional-surface parameter is determined based on the point position(s) such that the sectional surface includes at least one segment of a corresponding connecting line between an X-ray detector element associated with the particular measurement point and an X-ray source of the X-ray facility. For this purpose, recognition of the object and/or of a specific point on the object may be performed. For example, this may be effected by feature recognition in the X-ray image, for example, by identifying scale-invariant features. It is also possible, however, to segment the object in the X-ray image or to segment a plurality of regions in the X-ray image, and to perform a classification in order to recognize the object or certain parts of the object and identify therefrom specific features (e.g., the end of a catheter). Contrast-based segmentation may be performed, for example, by region growing.

The position of a relevant feature may correspond directly to the measurement point, or the measurement point may be offset with respect to this position. The offset may be made, for example, in a predetermined direction or according to the image data of the X-ray image. For example, for a catheter or another linear object, a position of the end of the catheter or object may initially be determined. Then, a longitudinal direction of the catheter or object may be determined. The measurement point may be offset in the longitudinal direction of the catheter or object by a predetermined distance from the previously determined position. In one embodiment, a plurality of measurement points may be selected. For example, two measurement points spaced apart in the longitudinal direction of an object may be selected. Since in this case a plurality of connecting lines are meant to lie in the sectional surface, in the case in which a sectional plane is used as the sectional surface, this is already fully defined by the selection of these two measurement points.

At least one direction vector may be determined in the X-ray image as the object information. The at least one direction vector specifies a direction defined with respect to the at least partial image of the object, whereby the sectional-surface parameter is determined based on the direction vector(s) such that at least one corresponding segment of the sectional surface in the acquisition space lies parallel to the corresponding direction vector or at a defined angle thereto.

Instead of determining a direction vector, two or more measurement points may be determined along this direction vector, and the sectional surface may be selected as explained previously such that the sectional surface includes the connecting line between the associated X-ray detector elements and the X-ray source. In the case that a sectional plane is chosen as the sectional surface, this lies parallel to the direction vector.

For a curved sectional surface, the direction vector may form a tangent to this sectional surface, in which case the direction vector touches the sectional surface, for example, at a plurality of preferably adjacent points.

A direction vector that corresponds to a longitudinal direction of a linear object (e.g., of a catheter) that is determined in the X-ray image may be selected as the direction vector. In this case, a sectional surface, of which at least part lies parallel to this longitudinal direction or at an angle thereto (e.g., perpendicular thereto), results.

The object may be a catheter. The position of a catheter tip is determined in the X-ray image, and the at least one measurement point lies at the position of the catheter tip or at another position defined with respect to the position of the catheter tip. Alternatively and additionally, the direction vector is directed in a longitudinal direction of the catheter. The longitudinal direction is determined from the X-ray image. A catheter tip may be the end of the catheter in a longitudinal direction. The determined longitudinal direction may be a local longitudinal direction at a certain position or in a certain segment of the catheter, for example, if the catheter is curved in the X-ray image. The longitudinal direction may be determined, for example, in the region of the catheter tip. A position of the catheter tip and a preferred direction (e.g., a longitudinal direction of the catheter in the region of the catheter tip) may be used as sectional-surface parameters, for example. Alternatively, a curved sectional surface, for example, may be used, in which case the sectional-surface parameter parameterizes the surface, such that the surface substantially follows the course of the catheter in the X-ray image.

A group of the acts that includes at least determining the particular sectional-surface parameter and controlling the magnetic resonance imaging facility to acquire the measurement data relating to the particular sectional surface may be repeated successively in time. In at least one of the repetitions, the particular sectional-surface parameter is determined based on the measurement data acquired in a corresponding earlier repetition. It is possible that the further acts of the method are also repeated, so that within each repetition or in some of the repetitions, X-ray images are additionally acquired in each case. From this, at least one piece of object information is determined. This allows implementation of slice repositioning in which both at least one piece of object information from a currently acquired X-ray image and the measurement data from a previous magnetic resonance imaging measurement may be taken into account for the purpose of slice repositioning.

Alternatively, the group may be repeated a plurality of times after each acquisition of a radiograph and determination of object information. This may be advantageous, for example, in order to reduce further an X-ray dose to which the acquisition volume is exposed and hence, for example, a radiation exposure of a patient. The sectional-surface parameter for a first sectional surface may be determined solely based on the object information, and a further repositioning may take into account the previously acquired measurement data. An X-ray image may be retaken, and object information may be determined at defined intervals in order to supply additional information to the repositioning. Repeating the group may also be used, however, as explained in greater detail below, to determine iteratively a sectional surface for which two-dimensional image data is acquired and/or calculated and, for example, displayed. For example, repeated acquisition of measurement data and subsequent adjustment of the sectional-surface parameter on the basis of this measurement data may be used to seek an optimum sectional-surface parameter, or an optimum slice, in which process a starting point for this search (e.g., an initial sectional-surface parameter) may be determined based on the object information and hence of the X-ray image. For example, the initial sectional-surface parameter may be determined, as explained above, such that the sectional surface includes a catheter tip or is positioned and/or orientated with respect to the catheter tip.

The measurement data acquired in the earlier repetitions may be used to image at least part of the object. Additional object information, which relates to the position and/or the orientation and/or the feature or at least one further feature of the object, is determined by processing this measurement data. The sectional-surface parameter is determined based on the additional object information. The additional object information may specify a point of intersection of the object with the sectional surface. In order to determine this point of intersection, two-dimensional image data may be determined from the measurement data (e.g., by a Fourier transform), and this two-dimensional image data may be segmented and/or feature recognition may be performed therein in order to identify the point of intersection. The sectional-surface parameter may be selected such that the sectional surface, the measurement data from which is subsequently acquired, includes the point of intersection and/or lies parallel or at a defined angle (e.g., perpendicular) to a connecting line between the point of intersection and another defined point (e.g., a catheter tip detected in the X-ray data).

During at least one of the repetitions, prior to determining the sectional-surface parameter, the magnetic resonance imaging facility may be controlled to acquire auxiliary measurement data relating to an auxiliary sectional surface. The auxiliary sectional surface is spaced apart from that sectional surface from which measurement data is acquired in the earlier repetition and/or lies at a defined angle to the surface. An auxiliary point of intersection of the object with the auxiliary sectional surface is determined, whereby the sectional-surface parameter is determined such that the sectional surface includes the point of intersection and the auxiliary point of intersection, or makes a defined angle (e.g., 90°) with a connecting line between the point of intersection and the auxiliary point of intersection. The auxiliary sectional surface may be selected based on the X-ray image and/or the object parameter. The described procedure may be used, for example, to determine very accurately the situation of a linear object (e.g., of a catheter that is not curved too severely), thereby making it possible to position and orientate the sectional surface very precisely with respect to this object.

The acts, or an additional group of acts that includes at least determining the relevant sectional-surface parameter and controlling the magnetic resonance imaging facility to acquire the relevant measurement data relating to the corresponding sectional surface, may be repeated if it is ascertained after acquiring the measurement data that the measurement data does not image the object, in which case the sectional-surface parameter is varied according to a preset model or a model defined based on the object information. Hence, varying the sectional-surface parameter may be used to search for a sectional surface that intersects or includes the object. In this case, when a sectional plane is used as the sectional surface, it is possible to vary in the acquisition space the position of the sectional surface (e.g., in a direction perpendicular to the sectional surface) and/or the orientation of the sectional surface. The object information may be taken into account, for example, in the form of determining from the X-ray data a longitudinal direction of the object, and making the displacements in this longitudinal direction and/or adjusting an orientation of the sectional surface as part of the variation such that it lies at an angle (e.g., perpendicular) to this direction.

If the measurement data images at least part of the object, the measurement data can be processed to determine imaging information that specifies what portion of the object is imaged by the measurement data, whereby, in the event that a repetition condition that evaluates the imaging information is satisfied, the steps, or a group of the steps that comprises at least determining the relevant sectional-surface parameter and controlling the magnetic resonance imaging facility to acquire the relevant measurement data relating to the corresponding sectional surface, are repeated, in which process the sectional-surface parameter is varied according to a preset model or a model defined on the basis of the object information and/or the measurement data, and in the event that the repetition condition is not satisfied, the two-dimensional image data is calculated on the basis of the previously acquired measurement data.

In particular, the sectional-surface parameter can be varied according to the imaging information in order to perform an optimization process, for instance, that maximizes the portion of the object that is imaged by the measurement data. A gradient technique, for example, can be performed for this purpose, in which the sectional-surface parameter is varied, for instance in order to vary an orientation and position of a sectional plane, and for a variation in two possible directions of variation it is determined for each degree of freedom in which direction the portion of the object that is imaged by the measurement data increases the most. The imaging information may be a numerical value, whereby it can be evaluated, for instance, directly in a gradient technique or another optimization technique. The imaging information, for example, may specify the size of the area that images the portion of the object in two-dimensional image data calculated from the measurement data. Alternatively, segments of the object can be defined, and how many of these segments are imaged by the measurement data can be determined. This can be effected, for instance, by defining features for the individual segments and checking whether each of these features is imaged by the measurement data. Prior knowledge, or a database storing data on the object, can be used to define the segmentation. Alternatively, segmentation of the object can also take place in the X-ray image.

The imaging information can be acquired directly in a k-space, i.e. a space of spatial frequencies, which is the space in which magnetic resonance measurement data is typically acquired. This is possible in cases in which unique features identifiable in k-space can be associated with individual segments of the object. Alternatively or additionally, temporary two-dimensional image data can be calculated from the measurement data, and the imaging information can be determined on the basis of this image data. In the event that the repetition condition is not satisfied, the temporary two-dimensional image data can be provided directly as the output two-dimensional image data.

Alternatively or additionally, the imaging information can be determined using a machine learning technique. For instance, a large amount of training data can be provided, which can match the format of the measurement data and indicates the different portions of a certain object or of an object of a certain type. Associated imaging information can be defined for this training data manually or by any other technique, and the training data annotated in this way can then be used for training a machine learning algorithm.

The imaging information can be determined on the basis of at least one feature of the object, which is specified by, or determined from, the object information and/or a prior knowledge of the object. In particular, the feature may be a shape of the object or of one or more segments of the object. It may also be, however, a template for template-based object recognition, a scale-invariant feature or the like. The relevant feature can be determined by segmenting the X-ray image. In this case, the X-ray image can be registered, in particular by rigid or non-rigid registration, to a dataset provided as the prior knowledge and specifying the object, for instance a dataset that is a 3D model of the object. This has the advantage that some features, for instance a basic shape of the object or of rigid regions of the object, are provided accurately by the prior knowledge, and additional information relating to a deformation, a position and/or an orientation of the object can be determined from the X-ray image.

A measure of what portion of the object is imaged by the measurement data can be determined as the imaging information, in which case the repetition condition compares the imaging information with a defined limit value or evaluates a convergence criterion, which takes into account a plurality of items of imaging information determined in successive repetitions of the group of steps. For instance it can be specified that at least 30, 50 or 70% of the object is imaged. Evaluating a convergence criterion is advantageous when an optimization technique is meant to be used in order to maximize the portion of the image that is imaged. The previously mentioned gradient technique may be such an optimization technique or iterative technique, for example.

In some cases, the object is meant to be guided to a defined destination point in the acquisition volume. Hence a destination point can be defined in the acquisition volume, with the sectional-surface parameter being determined such that the sectional surface comprises the destination point. A suitable destination point can be defined manually, for instance in three-dimensional magnetic resonance imaging data acquired previously in the same measurement geometry. It is also possible, however, to define the destination point in the X-ray image. For instance the sectional-surface parameter can be determined such that a sectional surface comprises a catheter tip of a catheter to be guided and a destination point to which the catheter is meant to be guided.

The sectional surface may be a sectional plane, wherein the sectional surface lies parallel to a central ray of an X-ray source of the X-ray facility. In the case of an approximately parallel X-ray beam, the sectional surface lies perpendicular to the image plane of the X-ray image and is imaged as a line in this image. For an X-ray source that emits a fan-shaped or conical beam, the ray that is emitted in the center of an emission surface is considered to be the central ray. For an X-ray source that is essentially a point source, the central ray can be the ray that is emitted at an angle equal to the average angle of radiation of the beam fan or beam cone.

An object acquisition facility can be used to determine position information that specifies the position of a marker element or position acquisition element arranged on the object in the acquisition volume, wherein the sectional-surface parameter is determined on the basis of the position information. Position information can be determined, for example, using radio-based triangulation or by sensors of the position acquisition element that detect the magnetic field. If the active instruments mentioned in the introduction are used, which provide position information for at least one of their points, this information can hence be taken into account in determining the sectional-surface parameter in the method according to the one or more of the present embodiments.

Two of the radiographs can be acquired at different acquisition angles, whereby a three-dimensional position in the acquisition volume is determined for at least one defined region of the object from the X-ray images as the object information, whereby the sectional-surface parameter is determined on the basis of the three-dimensional position. In particular, the sectional-surface parameter can be determined such that the sectional surface comprises the three-dimensional position. It is also possible that the sectional-surface parameter is defined such that the sectional surface is offset from the three-dimensional position in a defined direction. If additional three-dimensional positions are defined in the acquisition volume, for instance a destination position, the sectional-surface parameter can be defined such that the sectional surface has a defined orientation with respect to a straight connecting line between these positions, in particular runs parallel to the straight connecting line, where the straight connecting line in particular can lie in the sectional surface or lies perpendicular thereto.

An X-ray facility can be used that comprises a plurality of pairs of X-ray sources and X-ray detectors, the acquisition angles of which differ from one another, wherein the X-ray images acquired at the different acquisition angles are acquired by different pairs.

Alternatively, the radiographs acquired at the different acquisition angles can be captured by an X-ray facility that is mounted such that it can rotate and/or be displaced relative to the acquisition volume. The displacement and/or rotation of the X-ray facility can be detected, whereby the coordinate system used for the imaging by the X-ray facility can be registered both before and after the displacement and/or rotation to the coordinate system used for the imaging by the magnetic resonance imaging facility.

As already mentioned, a curved sectional surface can be used in the method according to one or more of the present embodiments. One possible way of implementing this is to perform the measurement data acquisition in a rectangular segment of the acquisition volume, which volume comprises the sectional surface. Then a volume reconstruction can be performed from three-dimensional image data, whereby the two-dimensional image data is read from the volume reconstruction along the curved sectional surface. It is thereby possible to read out the data for individual three-dimensional voxels directly, or interpolation can be performed for the individual image points between different voxels.

In the method according to one or more of the present embodiments, an X-ray facility can be used that comprises an X-ray detector and an X-ray source whose relative position and/or orientation can be varied with respect to the acquisition volume, wherein in the event of a user action to change the sectional surface acquired by the magnetic resonance imaging facility and/or in the event of a change to the sectional-surface parameter, the position and/or the orientation of the X-ray detector and/or of the X-ray source is automatically adjusted. The X-ray detector and the X-ray source can preferably be connected via a rigid mount, for instance a gantry or a C-arm, in order to displace and/or rotate said detector and source jointly. The position and/or orientation can be adjusted in particular such that the acquisition axis lies perpendicular to the sectional surface acquired by the magnetic resonance imaging facility.

The present embodiments relate not only to the method but also to a combined magnetic resonance imaging and X-ray apparatus that comprises a magnetic resonance imaging facility, an X-ray facility and a control facility, wherein the coordinate systems of said X-ray facility and said magnetic resonance imaging facility, which coordinate systems are used for imaging, are registered to each other by a mechanical coupling of the X-ray facility to the magnetic resonance imaging facility, wherein the control facility can implement the method according to any of the preceding claims. In addition, the magnetic resonance imaging facility and the X-ray facility are designed such that the method can be implemented.

The present embodiments also relate to a computer program, which can be loaded directly into a memory of a control facility of a combined magnetic resonance imaging and X-ray apparatus, which computer program comprises program means in order to implement the steps of the method when the computer program is executed in the control facility of the combined magnetic resonance imaging and X-ray apparatus.

The present embodiments also relate to an electronically readable data storage medium comprising electronically readable control information stored thereon, which comprises at least one computer program and is designed such that it performs the method when the data storage medium is used in a control facility of a combined magnetic resonance imaging and X-ray apparatus.

DETAILED DESCRIPTION

Figure 1:
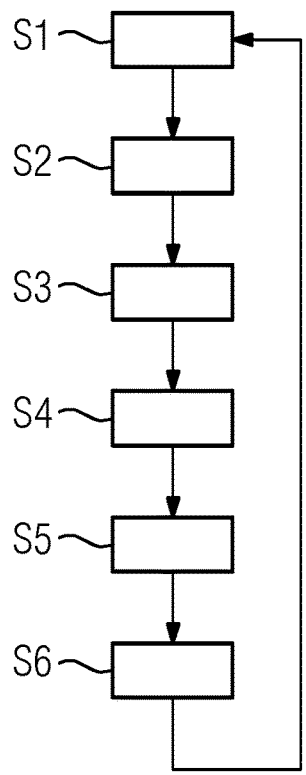
FIG. 1 shows schematically a flow diagram of an exemplary embodiment of a method.

FIG. 1 shows a flow diagram of an exemplary embodiment of a method for determining two-dimensional image data from at least one sectional surface of an acquisition volume as part of a magnetic resonance imaging process by a combined magnetic resonance imaging and X-ray apparatus. The imaging may be used to guide an object (e.g., a medical instrument such as a catheter) during an intervention. In this process, near real-time imaging at high image refresh rates may be implemented for a user. In order to achieve a high image refresh rate, magnetic resonance imaging may be performed only for one or a few sectional surfaces. In this case, the acquired and/or displayed sectional surfaces may be repositioned such that relevant sections may be shown to a user (e.g., the sections in which the guidance of the object may be seen). Thus, the sectional surface may be repositioned with a movement of the object in as short a time as possible.

In the method according to one or more of the present embodiments, a combined magnetic resonance imaging and X-ray apparatus is used. The combined magnetic resonance imaging and X-ray apparatus includes a magnetic resonance imaging facility and an X-ray facility. Coordinate systems of the magnetic resonance imaging facility and the X-ray facility used for imaging are registered to each other by a mechanical coupling of the X-ray facility to the magnetic resonance imaging facility. Such combined magnetic resonance imaging and X-ray apparatuses are explained in more detail later with reference to FIGS. 4 and 5. As a result of the known position and orientation of the coordinate systems with respect to each other, features acquired by the X-ray facility may be used to control the magnetic resonance imaging, because there is a defined relationship between the acquisition facilities.

In act S1, the X-ray facility is controlled to acquire at least one X-ray image that images at least part of the object. This is facilitated by selecting the acquisition region of the X-ray facility such that the object is located in the acquisition region.

Figure 2:
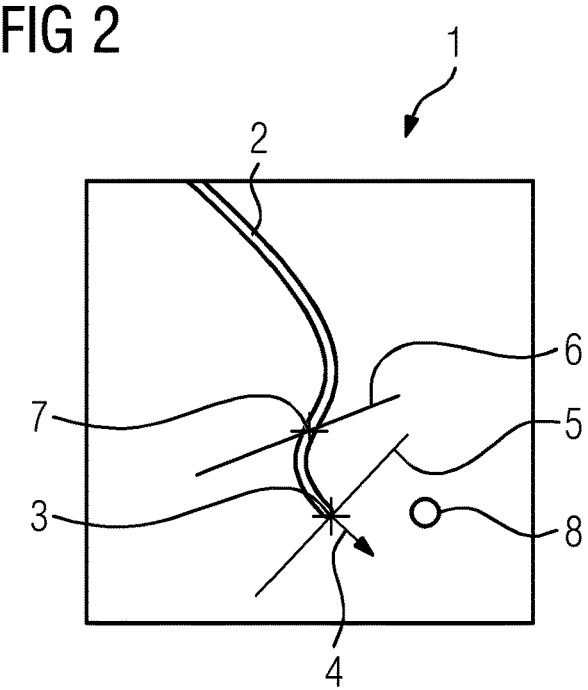
FIG. 2 shows schematically an X-ray image acquired in the method according to FIG. 1 and containing a superimposed possible sectional surface.

In act S2, image processing of the X-ray image is performed in order to determine at least one piece of object information relating to a position and/or an orientation and/or at least one feature of the object. FIG. 2 shows such an X-ray image 1 by way of example. The X-ray image 1 shows an object 2 (e.g., a catheter inserted into a patient). The other imaged objects (e.g., the bones of the patients) are not shown in FIG. 2 for reasons of clarity.

Two features may be determined from the X-ray image 1 (e.g., a point position 3 of a catheter tip and a direction vector 4) that specifies a longitudinal direction of the object 2 in the region of the catheter tip. The longitudinal direction is projected onto the plane of the X-ray image. In order to determine the point position 3, the object 2 is first segmented in the image data of the X-ray image 1. A number of segmentation algorithms known in the prior art may be used for this purpose. For example, a ridge detector may be used, and the object 2 may then be segmented by a region growing algorithm. After segmentation of the object 2, the end of the object 2 may be detected in an X-ray image 1 and defined as the point position 3. Alternatively, the point position 3 may, for example, be detected by feature detection (e.g., based on scale-invariant features). In addition, a longitudinal direction of the object 2 in the region of the catheter tip may be determined from the segmented object 2 (e.g., by calculating a center line of the object 2).

In act S3, slice parameters that define an arrangement of a sectional surface 5 in the acquisition volume are calculated from the point position 3 and the direction vector 4. A sectional plane is selected as the sectional surface, because the measurement data therefrom is particularly easy to acquire in the magnetic resonance imaging process. Thus, the sectional-surface parameters define a position and orientation of the sectional plane in space. These parameters are selected such that the sectional surface 5 includes at least part of a connecting line between the X-ray source and the X-ray detector element associated with the point position 3. It is thereby provided that the catheter tip lies in the sectional plane. In an alternative embodiment, the sectional-surface parameters may be selected such that the sectional plane 5 lies parallel to a central ray of an X-ray source. An offset of the sectional surface 5 in the plane of the X-ray image is determined based on the point position 3. This essentially corresponds to the previously described procedure if an x ray source having a substantially parallel X-ray beam is used or if the point position 3 lies close to the center of the acquisition region of the X-ray facility (e.g., something that may be provided by repositioning the X-ray facility) when there is a movement of the object 2, such that the catheter tip and hence the point position 3 lie in the central region of the X-ray image 1.

The sectional-surface parameters are additionally selected such that the direction vector 4 lies perpendicular to the sectional surface 5. The resultant two-dimensional image data thus shows a sectional surface at the instantaneous position of the catheter tip. The sectional surface lies perpendicular to the catheter tip at least in the image plane of the X-ray image. Alternatively or additionally, in order to acquire measurement data from another sectional surface, the sectional-surface parameters may be defined such that a point position that is offset with respect to the point position 3 in the direction of, or in the opposite direction from, the direction vector 4 is selected to measure a sectional surface that is offset from the sectional surface 5. This may be used, for example, to image a region into which the object 2 is introduced when the catheter is inserted further.

In act S4, the magnetic resonance facility is controlled to acquire measurement data relating to the sectional surface. Then in act S5, the two-dimensional image data is calculated from the measurement data and is then displayed in act S6. Acts S4 to S6 correspond to the usual procedure for acquiring two-dimensional measurement data by a magnetic resonance tomography system and are thus not explained in detail. The control of the magnetic resonance imaging facility in act S4 is performed based on the sectional-surface parameters, so that measurement data from the sectional surface 5 is acquired.

In some cases, two-dimensional image data may be imaged from a curved measurement surface. For example, the course of the catheter 2 may be determined, and the sectional surface may be taken along the course of the object 2, which is shown curved in FIG. 1. This is possible, for example, by controlling in act S4 the magnetic resonance imaging facility to acquire measurement data from a rectangular volume that includes the sectional surface. Volume imaging is thus performed on a potentially reduced acquisition volume. A three-dimensional image dataset may be generated from this measurement data in accordance with the usual procedure for volume imaging in the magnetic resonance tomography system, and specific measurement points are read out or interpolated from the dataset according to the defined curved sectional surface in order to calculate the two-dimensional image data.

As shown in FIG. 1, acts S1 to S6 are repeated in order to facilitate imaging that takes place in near real-time. For later repetitions, the sectional-surface parameter may be determined in act S3 based on the measurement data acquired in act S4 during earlier repetitions. If it is required, for example, to orientate the sectional surface 5 differently while intending that the surface still includes the catheter tip, then this is not possible in all cases when the sectional-surface parameters are determined solely from the X-ray image 1, or solely from the object information, because the X-ray image 1 does not provide any depth information for the point position 3. Relevant depth information may be determined, however, by taking into account the previously acquired measurement data. For example, the position at which the object 2 intersects the sectional surface 5 may be determined in the two-dimensional image data determined in act S5 of the previous repetition. Since the position of the sectional surface 5 in the acquisition volume is known, a three-dimensional position of the point of intersection and hence of the object 2 in the region of the sectional surface 5 may be determined therefrom. Hence, the sectional-surface parameters may be selected in the subsequent repetition such that this three-dimensional position lies within the sectional surface 5.

Two-dimensional image data from a sectional surface that is selected such that the object, at least in the region of an end (e.g., in the region of the catheter tip), runs within this sectional surface may be calculated and displayed. In addition, a destination point 8 may also be imaged in this sectional surface. Corresponding imaging may be achieved by a minor modification to the method explained with reference to FIG. 1. In this case, as explained earlier, the measurement data acquired in a previous repetition may be taken into account in order to determine a point of intersection 2 of the object with the sectional surface 5 of the previous repetition and hence to determine a three-dimensional position of the object 2. In order to locate a sectional surface in which the object 2 lies in the relevant region, an additional three-dimensional position of the object 2 may be determined. This is achieved by controlling the magnetic resonance imaging facility to acquire an auxiliary sectional surface 6 before determining the sectional-surface parameter in act S3. The auxiliary sectional surface 6 is determined based on the object information such that the auxiliary sectional surface 6 intersects the object 2. In addition, the auxiliary sectional surface 6 is offset from, and lies at an angle to, the sectional surface 5, the measurement data of which was acquired in the earlier repetition. As explained earlier for the sectional surface 5, a point of intersection of the object 2 with the auxiliary sectional surface 6 (e.g., the auxiliary point of intersection 7) is now determined.

Thus, two two-dimensional positions through which the sectional surface may run are known in the acquisition volume (e.g., the point of intersection of the object 2 with the sectional surface 5 and the auxiliary point of intersection 7 of the object 2 with the auxiliary sectional surface 6). If, in addition, the destination position 8 is defined as a three-dimensional destination position, then in act S3, the slice parameter may be defined such that the sectional surface, the measurement data from which is acquired in act S4, includes all three of these points. Thus, in the case of guiding a catheter, for example, it is possible to visualize within a sectional surface (e.g., a sectional plane) the catheter in the region of a tip of the catheter and the location to which the catheter may be guided.

Figure 3:
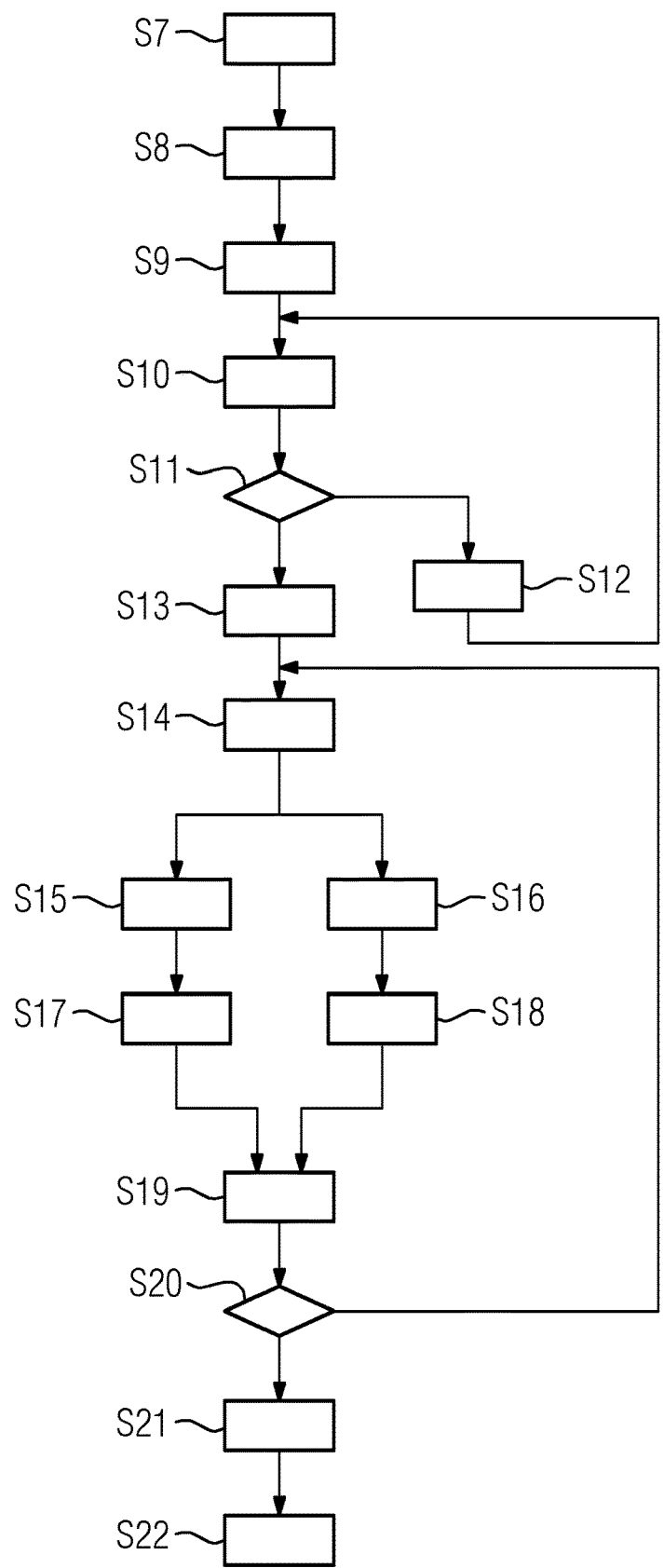
FIG. 3 shows schematically a flow diagram of another exemplary embodiment of the method.

FIG. 3 shows a flow diagram of another exemplary embodiment of a method for determining two-dimensional image data from at least one sectional surface of an acquisition volume as part of a magnetic resonance imaging process. As explained with reference to FIG. 1, the imaging may be performed with reference to an object. Acts S7 to S10 correspond to acts S1 to S4 in the method explained with reference to FIG. 1, where in act S7, an X-ray image is acquired, in act S8, image processing of the X-ray image is performed in order to determine object information, and in act S9, sectional-surface parameters are determined from this object information. Based on the parameters, measurement data is acquired in act S10 from the sectional surface parameterized by the sectional-surface parameters.

In act S11, it is determined whether the measurement data images at least part of the object. This may be effected, for example, by feature detection in the measurement data or in two-dimensional image data calculated from the measurement data. If this is not the case, then in act S12, new sectional-surface parameters are determined by varying the previous sectional-surface parameters, based on which the method is repeated from act S10. The slice parameters may be varied according to a preset model (e.g., a model that specifies a sequence of changes to the orientation and/or position of the sectional surface). In one embodiment, however, the variation depends on the object information determined in act S8, where, for example, the sectional-surface parameter may be varied such that the sectional surface is offset in a direction that is equal or opposite to a determined longitudinal direction of the object.

If it was established in act S11 that the measurement data images at least part of the object, then in acts S13 to S20, the imaging is optimized so as to maximize the portion of the object that is imaged by the measurement data. This is effected by a gradient technique in the exemplary embodiment, although other optimizations techniques may be used.

In act S14, a variation is performed for each degree of freedom (e.g., for each of the sectional-surface parameters), with, for example, two new values being generated for each sectional-surface parameter. One of the two values is slightly greater than the previous value, and one of the two values is slightly less than the previous value. The number of generated parameter sets, if all the sectional-surface parameters and hence all the degrees of freedom are varied simultaneously, equals $2^n$, where n is the number of sectional-surface parameters or degrees of freedom. If a large number of sectional-surface parameters are used, the variation may be restricted to a few of these parameters in order to reduce the resultant measurement and processing time and hence achieve a higher image refresh rate in the described method. For reasons of clarity, FIG. 3 depicts the described variation for only one degree of freedom, which results in only two branches in acts S15 to S18.

In each of acts S15 and S16, measurement data is acquired for a sectional surface parameterized by the respective values generated in act S14 for the sectional-surface parameter. Depending on the situation of these sectional surfaces and the specific design of the magnetic resonance imaging facility, it may be necessary to acquire the measurement data for the different sectional surfaces consecutively in time in acts S15 and S16.

In each of acts S17 and S18, for the measurement data determined respectively in act S15 and act S16, imaging information that specifies what portion of the object is imaged by the corresponding measurement data is determined. The imaging information may be determined, for example, by calculating from the measurement data in each case, two-dimensional image data, in which the object is segmented. The area of the segment associated with the object is provided as the imaging information. In an alternative embodiment, segmentation of the object may be defined, whereby it is determined how many of the segments are contained in the corresponding measurement data. This figure for the number of segments is provided as the imaging information. The object segmentation may be provided as prior knowledge (e.g., from a database that specifies medical instruments). It is also possible, however, to perform this segmentation in the X-ray image. In this case, segmentation in the X-ray image may also use prior knowledge (e.g., by elastic or rigid registration of the X-ray image to a three-dimensional dataset specifying the object). Feature recognition may be used to identify the segments of the object in the measurement data or in the image data calculated therefrom. In this case, the different segments may have the same or different features, because it is the number of segments imaged by the measurement data that is evaluated.

Another way of determining the imaging information is to use machine learning techniques. For example, an algorithm may be trained by a large number of training datasets, each of which images portions of the object. By manual or automatic annotation of this training data, each training dataset may be provided with information about the portion of the object that is imaged in the associated training dataset, or the value of the imaging information for the associated training dataset. This training data may be used to train an algorithm so as to be able to determine subsequently for the measurement data the imaging information that may be associated with each item of this measurement data.

Then in act S19, the set of measurement data containing the associated sectional-surface parameters for which the imaging information determined in acts S17 and S18, respectively, specifies imaging of a larger portion of the object is selected. Then in act S20, it is determined whether imaging information was already determined in a previous repetition of acts S14 to S19, and whether the new imaging information differs therefrom by a value that is less than a limit value. If this is the case, then it is assumed that the optimization technique performed in acts S14 to S20 has converged (e.g., that at least one local maximum of the portion of the object imaged by the measurement data has been reached). If this is the case, then in act S21, two-dimensional data is generated from the measurement data selected in act S19, and is displayed in act S22.

If no imaging information had been determined previously or the difference between successive imaging information was too large, then the method is continued from act S14, because it is assumed that an optimum portion for the imaging of the object has not been reached yet.

Figure 4:
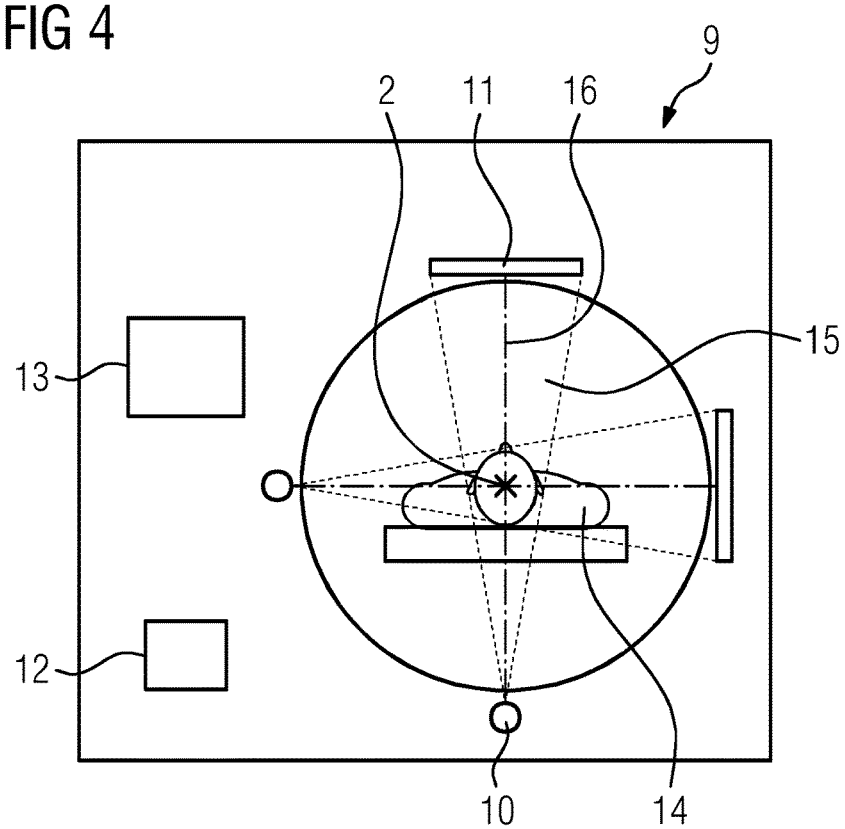
FIGS. 4 and 5 show schematically different exemplary embodiments of a combined magnetic resonance imaging and X-ray apparatus.

FIG. 4 shows an exemplary embodiment of a combined magnetic resonance imaging and X-ray apparatus includes a control facility 12 that may be configured to implement the method described with reference to FIG. 1 and/or the method described with reference to FIG. 3. To do this, the control facility 12 controls a magnetic resonance imaging facility including a plurality of coils for generating magnetic fields, although the coils are not shown for reasons of clarity. In addition, the control facility 12 controls an X-ray facility that includes the X-ray sources 10 and the X-ray detectors 11. The X-ray sources 10 emit X-ray radiation of conical beam geometry 15 that is substantially rotationally symmetrical about a central ray 16. The X-ray sources 10 and the X-ray detectors 11 are rigidly coupled to the components of the magnetic resonance imaging facility, whereby the coordinate systems of the X-ray facility and of the magnetic resonance imaging facility, which are used for imaging, are registered to each other. Alternatively, a common coordinate system may be used. The combined magnetic resonance imaging and X-ray apparatus 9 also includes a display facility 13 that may be used to output the two-dimensional image data, as explained with reference to FIG. 1 and FIG. 3.

Since there are two X-ray sources 10 and two X-ray detectors 11, which capture the object 2 from two acquisition angles (e.g., the object is represented as a cross for reasons of clarity and is inserted in a patient 14), an additional method for determining two-dimensional image data may be performed in addition to, or as an alternative to, the methods described in FIG. 1 and FIG. 3. In this method, two radiographs are acquired at different acquisition angles, whereby a three-dimensional position in the acquisition volume for at least one defined region of the object 2 is determined as the object information from the X-ray images. For example, a three-dimensional position of the catheter tip shown in FIG. 2 may be determined directly. Then the sectional-surface parameter is determined based on the three-dimensional position. The sectional-surface parameter may be determined such that the three-dimensional position lies within the sectional surface, or the sectional surface may be displaced and/or tilted in any way with respect to the three-dimensional position. In addition, a plurality of three-dimensional positions may be determined from the radiographs at different acquisition angles, all of which positions may lie within the sectional surface, for example.

Figure 5:
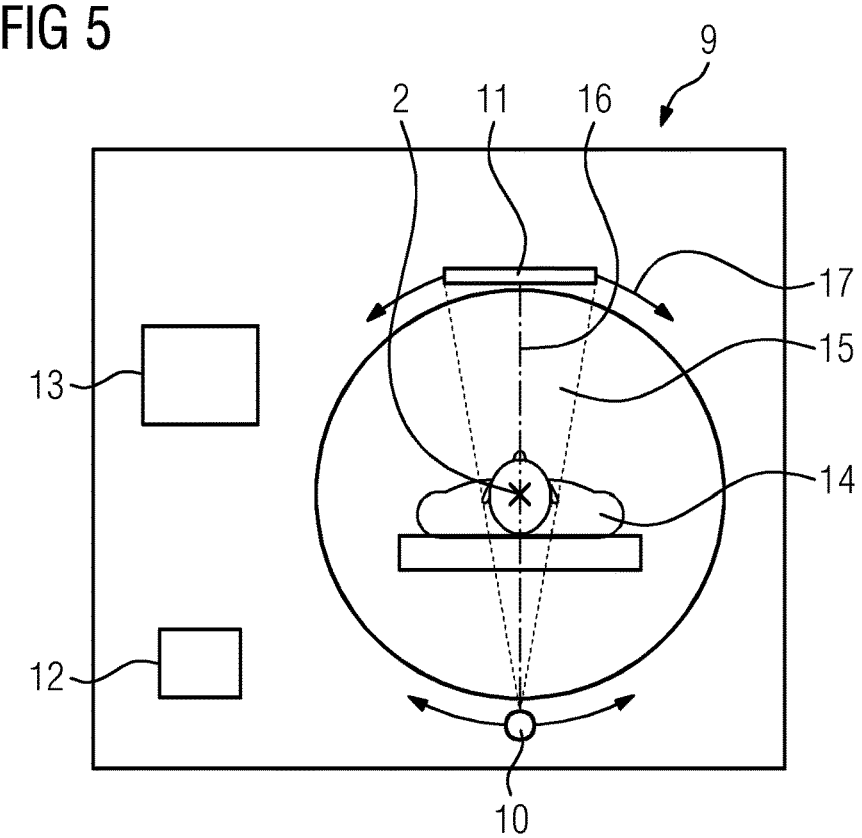

FIG. 5 shows another exemplary embodiment of a combined magnetic resonance imaging and X-ray apparatus 9. The configuration of the magnetic resonance imaging and X-ray apparatus 9 is substantially the same as the design described with reference to FIG. 4. The essential difference is that only one X-ray source 10 and one X-ray detector 11 are provided. The X-ray source 10 and the X-ray detector 11 may be rigidly coupled to the components of the magnetic resonance imaging facility, as described with reference to FIG. 4. This allows, for example, implementation of the exemplary embodiments of the method described with reference to FIG. 1 and FIG. 3, because these use only radiographs from a single perspective. In one embodiment, the X-ray source 10 and the X-ray detector 11 may be rotated jointly about the acquisition volume, as indicated by the arrows 17. This may be effected, for example, automatically by an actuator (not shown) that rotates a gantry (not shown) about the acquisition volume. The X-ray source 10 and the X-ray detector 11 are attached to the gantry. The degree of rotation may be detected and controlled by the control facility 12, so that despite the possible rotation, a registration between the coordinate systems used for imaging and the X-ray facilities and the magnetic resonance imaging facility is known in the control facility 12. If an X-ray apparatus of this type is used, which allows radiographs to be acquired at different acquisition angles, then the method variant described with respect to FIG. 4, in which at least one three-dimensional position is determined from a plurality of radiographs acquired at different acquisition angles, based on which the sectional-surface parameter is determined, may also be implemented. It may be sufficient in this case to vary the acquisition angle by a relatively small angle (e.g., five degrees or ten degrees). For example, the acquisition angle may be pivoted back and forth between two defined angles, with an X-ray image being acquired at each of the two return points.

A method described may also exist in the form of a computer program, which implements the method in a control facility 12 when the computer program is executed in the control facility 12. There may also be an electronically readable data storage medium (not shown) including electronically readable control information stored thereon. The information includes at least one computer program described and is configured such that the computer program performs the described method when the data storage medium is used in the control facility 12 of the combined magnetic resonance imaging and X-ray apparatus 9.

Although the invention has been illustrated and described in detail using the exemplary embodiments, the invention is not limited by the disclosed examples. A person skilled in the art may derive other variations therefrom that are still covered by the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining two-dimensional image data from at least one sectional surface of an acquisition volume as part of a magnetic resonance imaging process by a combined magnetic resonance imaging and X-ray apparatus, the combined magnetic resonance imaging and X-ray apparatus comprising a magnetic resonance imaging facility and an X-ray facility, wherein coordinate systems of the magnetic resonance imaging facility and the X-ray facility, respectively, that are used for imaging are registered to each other by a mechanical coupling of the X-ray facility to the magnetic resonance imaging facility, the method comprising:

acquiring, by a controller, an X-ray image that images at least part of an object, the object being a medical instrument inside a patient, the acquiring of the X-ray image comprising controlling the X-ray facility;

determining, by the controller, at least one piece of object information that relates to a position of the object, an orientation of the object, at least one feature of the object, or any combination thereof, the determining of the at least one piece of object information comprising image processing the X-ray image;

determining, by the controller, based on the at least one piece of object information, at least one sectional-surface parameter that defines an arrangement of the at least one sectional surface of the acquisition volume with respect to the at least partial image of the object in the X-ray image;

acquiring, by the controller, measurement data relating to the at least one sectional surface, the acquiring of the measurement data comprising controlling the magnetic resonance imaging facility; and calculating, by the controller, the two-dimensional image data from the measurement data, wherein the at least one sectional-surface parameter is used as the basis for the control of the magnetic resonance imaging facility, the calculation of the two-dimensional image data, or a combination thereof.

2. The method of claim 1, further comprising determining an associated point position of at least one measurement point in the X-ray image as the object information, the at least one measurement point being in a defined position with respect to the at least partial image of the object, wherein the at least one sectional-surface parameter is determined based on the associated point position or the associated point positions such that the at least one sectional surface comprises at least one segment of a corresponding connecting line between an X-ray detector element associated with the particular measurement point and an X-ray source of the X-ray facility.

3. The method of claim 1, further comprising determining at least one direction vector in the X-ray image as the object information, the at least one direction vector specifying a direction defined with respect to the at least partial image of the object, wherein the at least one sectional-surface parameter is determined based on the at least one direction vector such that at least one corresponding segment of the at least one sectional surface in an acquisition space lies parallel to a corresponding direction vector or at a defined angle thereto.

4. The method of claim 3, wherein the object is a catheter, wherein the method further comprises determining a position of a catheter tip in the X-ray image, and wherein the at least one measurement point lies at a position of the catheter tip or at another position defined with respect to the position of the catheter tip, the at least one direction vector is directed in a longitudinal direction of the catheter, the longitudinal direction of the catheter being determined from the X-ray image, or a combination thereof.

5. The method of claim 1, wherein the determining of the at least one sectional-surface parameter and the controlling of the magnetic resonance imaging facility to acquire the measurement data relating to the at least one sectional surface is repeated successively in time, and wherein in at least one of the repetitions, the at least one sectional-surface parameter is determined based on the measurement data acquired in a corresponding earlier repetition.

6. The method of claim 5, wherein the measurement data acquired in the earlier repetitions is used to image at least part of the object, wherein the method further comprises determining additional object information that relates to the position, the orientation, the at least one feature of the object, or any combination thereof, or at least one further feature of the object, the determining of the additional object information comprising processing the measurement data, the at least one sectional-surface parameter being determined based on the additional object information.

7. The method of claim 6, wherein the additional object information specifies a point of intersection of the object with the at least one sectional surface.

8. The method of claim 7, wherein during at least one of the repetitions, prior to determining the at least one sectional-surface parameter, the magnetic resonance imaging facility is controlled to acquire auxiliary measurement data relating to an auxiliary sectional surface, wherein the auxiliary sectional surface is spaced apart from the sectional surface from which measurement data is acquired in an earlier repetition, the auxiliary section surface lies at a defined angle to the sectional surface from which measurement data is acquired in the earlier repetition, or a combination thereof, wherein an auxiliary point of intersection of the object with the auxiliary sectional surface is determined, wherein the at least one sectional-surface parameter is determined such that the at least one sectional surface comprises the point of intersection and the auxiliary point of intersection, or makes a defined angle with a connecting line between the point of intersection and the auxiliary point of intersection.

9. The method of claim 1, wherein the determining of the relevant sectional-surface parameter and the controlling of the magnetic resonance imaging facility to acquire the relevant measurement data relating to the corresponding sectional surface are repeated when it is ascertained, after acquiring the measurement data, that the measurement data does not image the object, in which case the sectional-surface parameter is varied according to a preset model or a model defined based on the object information.

10. The method of claim 1, further comprising determining imaging information that specifies what portion of the object is imaged by the measurement data when the measurement data images at least part of the object, the determining of the imaging information that specifies what portion of the object is imaged by the measurement data comprising processing the measurement data, wherein, in the event that a repetition condition that evaluates the imaging information is satisfied, a group of acts including the determining of the relevant sectional-surface parameter and the controlling of the magnetic resonance imaging facility to acquire the relevant measurement data relating to the corresponding sectional surface is repeated, and wherein the sectional-surface parameter is varied according to a preset model or a model defined based on the object information, the measurement data, or a combination thereof, and in the event that the repetition condition is not satisfied, the two-dimensional image data is calculated based on the previously acquired measurement data.

11. The method of claim 10, wherein the imaging information is determined based on at least one feature of the object that is specified by, or determined from, the object information, a prior knowledge of the object, or a combination thereof.

12. The method of claim 10, wherein a measure of what portion of the object is imaged by the measurement data is determined as the imaging information, wherein the repetition condition compares the imaging information with a defined limit value or evaluates a convergence criterion that takes into account a plurality of items of imaging information determined in successive repetitions of the group of acts.

13. The method of claim 1, further comprising defining a destination point in the acquisition volume, with the at least one sectional-surface parameter being determined such that the at least one sectional surface comprises the destination point.

14. The method of claim 1, wherein the at least one sectional surface is a sectional plane, and wherein the sectional surface lies parallel to a central ray of an X-ray source of the X-ray facility.

15. The method of claim 1, wherein an object acquisition facility is usable to determine position information that specifies the position of a marker element or position acquisition element arranged on the object in the acquisition volume, and wherein the at least one sectional-surface parameter is determined based on the position information.

16. The method of claim 1, wherein two X-ray images are acquired at different acquisition angles, wherein a three-dimensional position in the acquisition volume is determined for at least one defined region of the object from the two X-ray images as the object information, and wherein the at least one sectional-surface parameter is determined based on the three-dimensional position.

17. The method of claim 16, wherein the X-ray facility comprises a plurality of pairs of X-ray sources and X-ray detectors, acquisition angles of which differ from one another, and wherein the two X-ray images acquired at the different acquisition angles are acquired by different pairs of the plurality of pairs of X-ray sources and X-ray detectors.

18. The method of claim 16, wherein the two X-ray images acquired at the different acquisition angles are captured by the X-ray facility, which is mounted such that the X-ray facility is rotatable, displaceable, or rotatable and displaceable relative to the acquisition volume.

19. The method of claim 1, wherein a curved sectional surface is used.

20. The method of claim 1, wherein the X-ray facility comprises an X-ray detector and an X-ray source, a relative position, orientation, or position and orientation of the X-ray facility being variable with respect to the acquisition volume, wherein in the event of a user action to change the sectional surface acquired by the magnetic resonance imaging facility, in the event of a change to the sectional-surface parameter, or a combination thereof, the position, the orientation, or any combination thereof of the X-ray detector, the X-ray source, or the X-ray detector and the X-ray source is automatically adjusted.

21. A combined magnetic resonance imaging and X-ray apparatus comprising:
 a magnetic resonance imaging facility;
 an X-ray facility; and
 a controller,
 wherein coordinate systems of the X-ray facility and the magnetic resonance imaging facility used for imaging, respectively, are registered to each other by a mechanical coupling of the X-ray facility to the magnetic resonance imaging facility, and
 wherein the controller is configured to:
  determine two-dimensional image data from at least one sectional surface of an acquisition volume as part of a magnetic resonance imaging process, the determination of the two-dimensional image data comprising:
   acquisition of at least one X-ray image that images at least part of an object inside a patient, the acquisition of the at least one X-ray image comprising control of the X-ray facility;
   determination of at least one piece of object information that relates to a position of the object, an orientation of the object, at least one feature of the object, or any combination thereof, the determination of the at least one piece of object information comprising image processing the at least one X-ray image;
   determination of, based on the at least one piece of object information, at least one sectional-surface parameter that defines an arrangement of the at least one sectional surface of the acquisition volume with respect to the at least partial image of the object in the at least one X-ray image;
   acquisition of measurement data relating to the at least one sectional surface, the acquisition of the measurement data comprising control of the magnetic resonance imaging facility; and
   calculation of the two-dimensional image data from the measurement data,
  wherein the at least one sectional-surface parameter is used as the basis for the control of the magnetic resonance imaging facility, the calculation of the two-dimensional image data, or a combination thereof.

22. In a non-transitory computer-readable storage medium storing instructions executable by a controller of a combined magnetic resonance imaging and X-ray apparatus to determine two-dimensional image data from at least one sectional surface of an acquisition volume as part of a magnetic resonance imaging process, the combined magnetic resonance imaging and X-ray apparatus comprising a magnetic resonance imaging facility and an X-ray facility, wherein coordinate systems of the magnetic resonance imaging facility and the X-ray facility, respectively, that are used for imaging are registered to each other by a mechanical coupling of the X-ray facility to the magnetic resonance imaging facility, the instructions comprising:
 acquiring, by the controller, at least one X-ray image that images at least part of an object inside a patient, the acquiring of the at least one X-ray image comprising controlling the X-ray facility;

determining, by the controller, at least one piece of object information that relates to a position of the object, an orientation of the object, at least one feature of the object, or any combination thereof, the determining of the at least one piece of object information comprising image processing the at least one X-ray image;

determining, by the controller, based on the at least one piece of object information, at least one sectional-surface parameter that defines an arrangement of the at least one sectional surface of the acquisition volume with respect to the at least partial image of the object in the at least one X-ray image;

acquiring, by the controller, measurement data relating to the at least one sectional surface, the acquiring of the measurement data comprising controlling the magnetic resonance imaging facility; and calculating, by the controller, the two-dimensional image data from the measurement data, wherein the at least one sectional-surface parameter is used as the basis for the control of the magnetic resonance imaging facility, the calculation of the two-dimensional image data, or a combination thereof.

\* \* \* \* \*